(12) United States Patent
Tavor et al.

(10) Patent No.: US 10,945,595 B2
(45) Date of Patent: Mar. 16, 2021

(54) DENTAL SUCTION-MIRROR TOOL

(71) Applicant: RNDENT IP LTD., Hod Haharon (IL)

(72) Inventors: David Tavor, Hod Hasharon (IL); Nissim Avramov, Tel Aviv (IL); Roee Haimovich, Nesher (IL)

(73) Assignee: RNDENT IP LTD., Hod Hasharon (IL)

( * ) Notice: Subject to any disclaimer, the term of this patent is extended or adjusted under 35 U.S.C. 154(b) by 32 days.

(21) Appl. No.: 16/447,570

(22) Filed: Jun. 20, 2019

(65) Prior Publication Data

US 2019/0298163 A1    Oct. 3, 2019

Related U.S. Application Data

(63) Continuation-in-part of application No. 15/736,153, filed as application No. PCT/IL2016/050627 on Jun. 15, 2016, now abandoned.

(30) Foreign Application Priority Data

Jun. 22, 2015  (IL) .......................................... 239582

(51) Int. Cl.
   *A61B 1/247*  (2006.01)
   *A61C 17/08*  (2006.01)
   *A61B 17/00*  (2006.01)
   *A61C 17/02*  (2006.01)

(52) U.S. Cl.
   CPC .............. *A61B 1/247* (2013.01); *A61C 17/08* (2019.05); *A61B 2017/0023* (2013.01); *A61C 17/0208* (2013.01); *A61M 2210/0625* (2013.01)

(58) Field of Classification Search
   CPC ..... A61C 17/08; A61C 17/088; A61C 17/092; A61C 17/0208; A61C 17/043; A61B 1/247; A61B 1/253; A61B 1/24; A61B 1/126; A61B 1/127; A61B 1/00094
   See application file for complete search history.

(56) References Cited

U.S. PATENT DOCUMENTS

| 320,075    | A |   | 6/1885 | Littlefield |                     |
|------------|---|---|--------|-------------|---------------------|
| 3,052,031  | A | * | 9/1962 | Piscitelli  | ........ A61B 1/253 |
|            |   |   |        |             | 433/30              |
| 3,091,034  | A | * | 5/1963 | Piscitelli  | ........ A61B 1/253 |
|            |   |   |        |             | 433/30              |
| 3,092,910  | A | * | 6/1963 | Warriner    | ........ A61C 17/08 |
|            |   |   |        |             | 433/31              |

(Continued)

FOREIGN PATENT DOCUMENTS

| CN | 1276192   | 12/2000 |
| CN | 201101520 | 8/2007  |

(Continued)

OTHER PUBLICATIONS

USPTO; Non-Final Office Action dated May 11, 2018 in U.S. Appl. No. 15/736,153.

(Continued)

*Primary Examiner* — Jacqueline T Johanas
*Assistant Examiner* — Shannel Nicole Belk
(74) *Attorney, Agent, or Firm* — Snell & Wilmer L.L.P.

(57) ABSTRACT

The invention provides a disposable dental mirror tool combined with a disposable suction means, enabling simultaneously viewing the patient's mouth and cleaning liquids and debris formed during dental procedures.

9 Claims, 5 Drawing Sheets

(56) References Cited

U.S. PATENT DOCUMENTS

| | | | |
|---|---|---|---|
| 3,102,338 A | | 9/1963 | Warriner |
| 3,829,199 A | | 8/1974 | Brown |
| 3,928,916 A | * | 12/1975 | Hansson ................ A61B 1/247 433/31 |
| 3,986,266 A | | 10/1976 | Vellendar |
| 4,279,594 A | * | 7/1981 | Rigutto ................ A61B 1/253 433/31 |
| 4,521,185 A | | 6/1985 | Cohen |
| 4,925,391 A | | 5/1990 | Berlin |
| 5,139,420 A | | 8/1992 | Walker |
| 5,230,622 A | | 7/1993 | Brossoit |
| 5,449,290 A | | 9/1995 | Reitz |
| 6,050,939 A | | 4/2000 | Pak Wai |
| 6,142,777 A | * | 11/2000 | Winston ................ A61B 1/253 433/30 |
| 6,247,924 B1 | | 6/2001 | Gunnarsson |
| 6,575,744 B1 | | 6/2003 | Oshida |
| 7,553,158 B2 | | 6/2009 | Frider et al. |
| 8,133,052 B1 | * | 3/2012 | Emmons, III ..... A61B 1/00096 433/30 |
| 2004/0115588 A1 | | 6/2004 | Sommers |
| 2007/0122765 A1 | | 5/2007 | Nyman |
| 2009/0311648 A1 | | 12/2009 | Clasen |
| 2010/0021860 A1 | * | 1/2010 | Christman ............. A61C 17/08 433/96 |
| 2010/0021863 A1 | | 1/2010 | Braman |
| 2012/0021373 A1 | | 1/2012 | Moreno |
| 2016/0227987 A1 | | 8/2016 | Clasen |

FOREIGN PATENT DOCUMENTS

| | | | |
|---|---|---|---|
| CN | 102835946 | 6/2011 | |
| DE | 19846298 | 2/2004 | |
| DE | 19846298 B4 * | 2/2004 | ............. A61C 17/08 |
| EP | 0314657 A1 * | 5/1989 | ............. A61C 17/08 |
| FR | 2595939 | 9/1987 | |
| FR | 2678156 | 12/1992 | |
| GB | 1255719 | 12/1971 | |
| JP | 4505615 B2 * | 7/2010 | ............. A61B 1/253 |
| WO | WO00/60997 A1 | 10/2000 | |
| WO | 2014140795 | 9/2014 | |

OTHER PUBLICATIONS

USPTO; Final Office Action dated Aug. 28, 2018 in U.S. Appl. No. 15/736,153.

USPTO; Advisory Action dated Nov. 19, 2018 in U.S. Appl. No. 15/736,153.

USPTO; Non-Final Office Action dated Dec. 13, 2018 in U.S. Appl. No. 15/736,153.

USPTO; Final Office Action dated Apr. 3, 2019 in U.S. Appl. No. 15/736,153.

European Search report in Application No. 16813840.0 dated Jan. 25, 2019.

CN Office Action dated Mar. 2, 2020 in Chinese Application No. 201680036451.8.

* cited by examiner

DENTAL SUCTION-MIRROR TOOL

CROSS REFERENCE TO RELATED APPLICATIONS

This application is a continuation-in-part of U.S. patent application Ser. No. 15/736,153, filed on Dec. 13, 2017, and entitled "NEW DENTAL SUCTION-MIRROR TOOL" which is a national stage entry of International Application No. PCT/IL2016/050627, entitled "NEW DENTAL SUCTION-MIRROR TOOL" filed on Jun. 15, 2016, which claims priority to and the benefit of Israel Patent Application Number 239582, filed Jun. 22, 2015, the disclosures of which are incorporated herein by reference to the extent such disclosures do not conflict with the present disclosure.

FIELD OF THE INVENTION

The present invention relates to the field of dental treatment in general, and to a new design of disposable dental mirror tool combined with a dental suction mechanism, in particular.

BACKGROUND OF THE INVENTION

Various dental mirrors have been used by dentists for many years in order to view inside a patient's mouth. The dental mirrors consist of a small cylindrical metal shaft with a metal disk attached at the end of it, which holds the mirror. Typically, such mirrors are biologically inert, environmentally stable and durable, and are capable of being autoclaved and sterilised, or are disposable.

However, being disposable or not, the dental mirrors have an essential drawback in their design. The reflective surface of the small hand-held dental mirrors become instantly fogged due to moisture and heat in the patient's mouth, or the surface of the mirrors becomes non-reflective due to saliva and debris from drilling operations and other dental procedures.

The conventional method for cleaning the debris formed during the dental procedure is by using a suction tube hold in another hand, which does not hold the mirror, or the hands of an assistant, In addition, the assistant or the dentist uses cloth to remove fog, saliva and debris from the mirror, or by spraying water on the mirror tool. Such method for cleaning the debris and dental mirror is wasteful in terms of time and effort and makes the dental surgeon's work more cumbersome. Therefore, there is a long-felt need for improvement through the invention of a mechanism or new tool that would simultaneously allow a dentist using only one hand to view in a patient's mouth and effectively clean the debris and the mirror to achieve an operable reflection without having to remove the mirror from the patient's mouth for either cleaning or replacement. This would allow a streamlined, fast and more convenient procedure in a dentist's office for the benefit of both the dentist and the patient. In addition, to increase ergonomics and user-friendliness, such a device should be able to be operated by the dentist in the same hand that normally holds the mirror during dental procedures.

There are some known pre-existing solutions to the problem of designing a dental mirror cleaning device. U.S. D 0,320,075 shows an instrument for dental care which includes a handle having a mirror at one end and includes provision for enabling suction and water syringe operations via passage from one end to the other end of the instrument.

U.S. Pat. No. 7,553,158 describes a dental evacuation tool suitable to be placed in fluid communication with a dental vacuum source. The tool comprises a suction head and an elongated tubular handle.

U.S. Pat. No. 3,102,338 relates to a dental mirror for use in combination with a fluid-cooled drill which will evacuate fluid from the patient's mouth, which maintains the reflecting surface of the mirror free of the coolant during use.

U.S. Pat. No. 3,986,266 discloses a dental mirror comprising a handle with a reflecting mirror mounted at one end, an air jet tube secured to the handle and arranged to direct a flow of air onto the reflecting face of the mirror, and including a water supply tube from which droplets of water are supplied into the air stream from the air jet tube.

The above designs and devices are feasible, but lacking in one aspect or another. Some of them require an air and water line simultaneously connected to the mirror hand-piece to allow water and air continuously flow over the mirror surface, removing the opportunity for debris to accumulate. Others require sterilization, and all present various drawbacks. Thus, there is a clear demand for the essential improvement of the current dental mirror tool.

SUMMARY OF THE INVENTION

The invention provides a disposable dental suction anti-fog mirror tool not requiring sterilization, configured to be manipulated by one hand and to free the second hand of a dentist or a hand of an assistant during a dental procedure, allowing the dentist a clear view of patient's mouth, without having to remove the mirror from the mouth for cleaning from saliva with debris or from fog caused by moist and heat, comprising i) a mirror frame 1 made of a single plastic piece shaped to comprise a) a circular section 11 for accommodating a circular mirror, defining a mirror plane; b) an oblong opening 7 adjacent to said round section for evacuating fluids from said mirror, defining a front part of said frame; c) a cylindrical suction tube base 3 for inserting into a standard dental suction tube, the tube serving as a handle and connecting said dental tool with a vacuum source, said cylinder and said mirror plane forming an angle of between 50° and 60°; and d) a circular back opening 8 for evacuating fluids from behind and beneath said frame, defining a backside part of said frame; ii) a frame bottom 10 having a circular edge, located in said circular section for supporting said mirror; and iii) a planar anti-fog mirror 2 to be attached on said frame bottom in said circular section; said angle and said openings allowing for optimal liquid flow relative to the mirror plane and for effectively removing fluids and debris created during said dental procedure, thereby preventing the mirror from becoming non-reflective. In some embodiments, said frame and said frame bottom constitute an integrated disposable plastic unit. Said frame bottom may be held in said round section of the frame by glue or by welding, for example by ultrasonic welding method. Said mirror may comprise an adhesive layer located on the side not used for reflecting light and may be attached to said frame bottom by said adhesive layer; the adhesive layer may be realized by a layer of stable glue or a sticker of a suitable shape. In other embodiments, said mirror may be held in said frame by arresting means, such as ribs that stop and prevent the mirror from falling out of the frame, or such as snaps catching the mirror and holding it within the frame. Said front opening efficiently evacuates liquids from the surface of said mirror, and said back opening prevents accumulation of liquids below the tool and sudden immersion of the mirror surface. In one embodiment of the invention, said mirror has a smaller diameter than said frame circular section into which it is set, allowing sucked liquid to move also between the mirror edge and the frame to below the mirror surface, said frame bottom further being provided with a circular ridge, concentric with said circular edge and elevated toward the mirror; said mirror sits on the ridge, creating a free space between said mirror and said bottom, wherein a part of the sucked liquid moves from above the mirror surface via said space and via said front oblong opening to the suction tube. The clearance between said mirror edge and the frame in said circular section, for example about 0.2-1.5 mm such as about 1 mm, enables the sucked liquid to seep from above the mirror surface down around the whole circumference of the mirror.

The present invention relates to a dental suction-mirror tool comprising a mirror frame with a disposable mirror, characterised in that said tool is capable of being attached onto a dental suction tube at an angle of about 50-60° relative to the mirror plane. The dental suction tube can be any standard dental suction tube used during dental procedures. It can be either an integral part of the dental suction-mirror tool, or attached onto said tool when needed.

A further aspect of the present invention is that the dental mirror tool is disposable. The disposable adhesive and anti-fog mirror is attached to the mirror frame. The mirror can be made of a clear and highly reflective thermoplastic polymer, for example glycol-modified polyethylene terephthalate (PETG).

Another aspect of the present invention is a method of removing liquids and debris during dental procedures while simultaneously viewing the patient's mouth with an anti-fog mirror, without having to remove the mirror for cleaning.

Various embodiments of the invention may allow various benefits, and may be used in conjunction with various applications. The details of one or more embodiments are set forth in the accompanying figures and the description below. Other features, objects and advantages of the described techniques will be apparent from the description and drawings and from the claims.

BRIEF DESCRIPTION OF THE DRAWINGS

The present invention will be understood and appreciated more fully from the following detailed description taken in conjunction with the appended figures.

FIG. 2 is a top view (FIG. 2A) and side view (FIG. 2B) of the dental suction-mirror tool.

DETAILED DESCRIPTION OF THE INVENTION

In the following description, various aspects of the invention will be described. For purposes of explanation, specific configurations and details are set forth in order to provide a thorough understanding of the invention. However, it will also be apparent to one skilled in the art that the invention may be practiced without the specific details presented herein. Furthermore, well-known features may be omitted or simplified in order not to obscure the invention.

The present invention relates to a dental suction-mirror tool comprising a mirror frame with a disposable mirror and a suction tube base shaped as a cylinder, characterised in that said tool is configured to be attached onto a dental suction tube at an angle of about 50-60° relative to the mirror plane. The cylindrical dental suction tube base can accept any standard dental suction tube used during the dental procedures. Said suction tube can be either an integral part of the dental suction-mirror tool, or it can be connected with said tool by slipping over said cylindrical suction tube base when needed.

The dental suction mirror tool of the invention is suitably sized, weighted and configured to be held in a dentist's hand during use, and to be manipulated by only one hand during the dental procedure. In fact, the dental suction mirror tool of the invention replaces the pair of tools, namely the mirror and the suction tube, which are used by any dentist today. This makes possible for a dentist to work without employing an assistant, who at the same time might be able to prepare the next step of the treatment independently. That would significantly reduce valuable time of the dental procedures. In addition, simultaneous use of the mirror and suction tool combined in one single instrument allows a dentist cleaning the debris formed during the dental procedure effectively and comfortably for a patient. This is because the dentist, who sees the treated area, knows exactly where and at which angle, the tool should be held and when the suction should be applied.

Thus, it is the object of the present invention to combine the dental mirror and suction tube in a single, one-hand-held instrument to allow a dentist to simultaneously view and clean the treated area without changing dental tools or interrupting the dental procedure.

Figure 1:
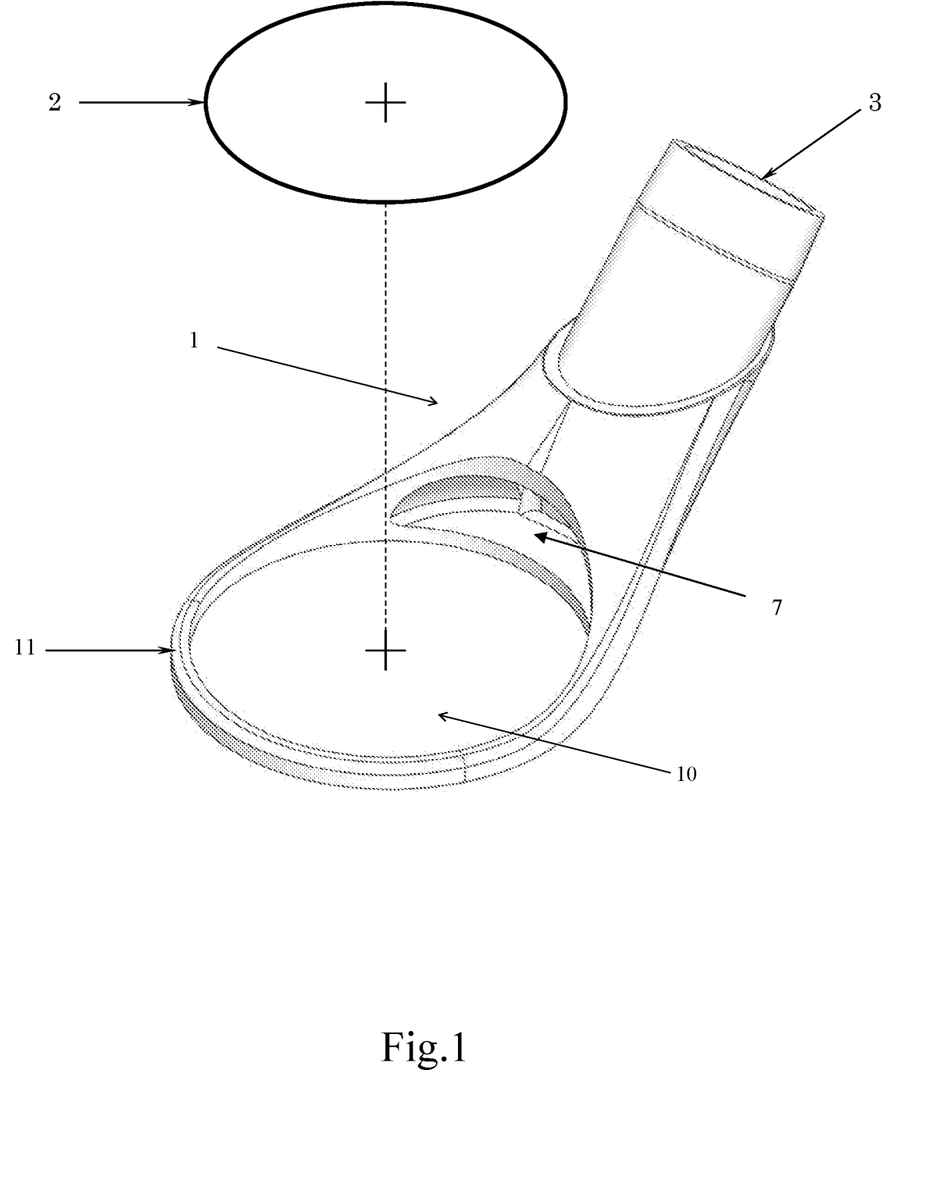
FIG. 1 is a perspective view of the disposable dental suction-mirror tool in one embodiment of the invention.

Reference is now made to FIG. 1 showing the perspective, top and front view of the new dental suction-mirror tool of the present invention in one embodiment. As shown in FIG. 1, disposable mirror 2 can be attached to mirror frame 1 from above or via bottom 10, which may be an integral part of the mirror frame, or may be constituted by a separable member (10 in FIG. 4), possibly attachable to the frame by welding, such as ultrasonic welding; wherein said mirror may be adhesive or may be held on said bottom by snaps 9. Mirror frame 1 comprises an essentially round section 11 and a specifically designed bent structure ending with a cylindrical shape 3 for the reasons explained below. Mirror frame 1 forms a direct support structure for disposable mirror 2. Any disposable dental suction tube (for example as 4 shown in FIG. 3), which is available in the dentist's office, can be easily slipped on said cylindrical base 3 and said mirror frame 1 at an angle of about 50°-60° relative to the mirror plane, shown as 5 in FIG. 2B. Suction tube 4 may serve as a handle for the dental suction-mirror tool.

Figure 2A:
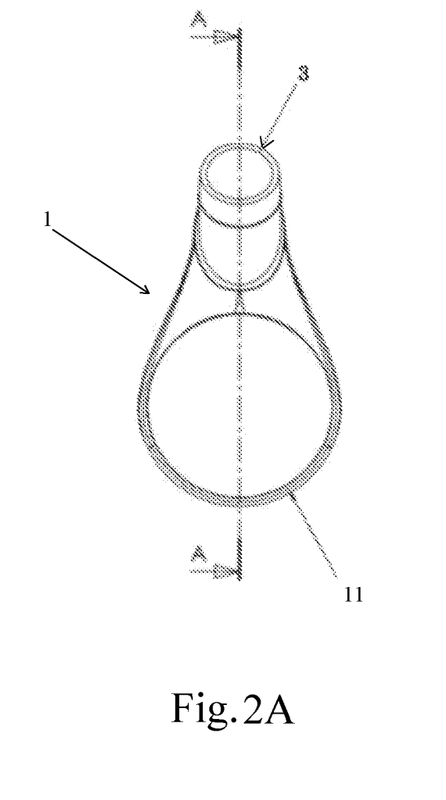
Figure 2B:
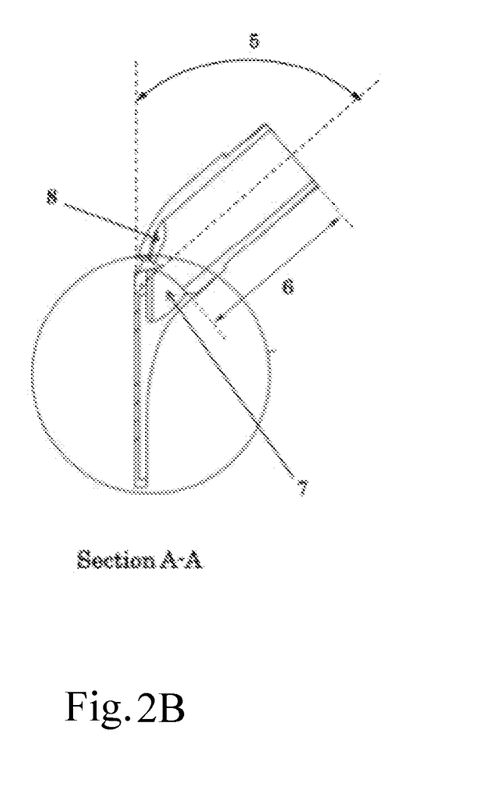

As shown in FIG. 2, due to the very special design of the tool, a suction tube can be connected with the mirror frame 1, via said cylindrical suction tube base, only at specific angle (5 shown in FIG. 2B) between the mirror plane and the longitudinal axis of the cylinder and the tube. Rotating the suction tube 4 shown in FIG. 3 with the dental suction-mirror tool makes it possible to rotate the mirror in the patient's mouth in order to attain the required view. Angle 5, providing free flow zone 6 for the liquid removed via suction tube base 3 constitutes one of the major aspects of the present invention. According to empirical considerations, optimal liquid flow via suction tube base 3 occurred when angle 5 was about 50-60°, preferably 50°-55°, relative to the mirror plane. The term "optimal" means that the debris created during the dental procedure is effectively removed from the mirror surface. Together with said specific angle, two specifically located openings for evacuating fluids make the tool very efficient: a first opening 7, front one, broader and oblong, adjacent to the mirror surface, evacuates fluids across the mirror, a second opening 8, back one, round and narrower, evacuates fluids from behind and below the tool, when the tool is oriented with the mirror up.

Suction tube base 3 has standard size and dimensions to be compatible with suction tubes used in dentistry. The suction tube can be easily attached to the mirror frame via said cylindrical suction tube base, allowing an effective suction of the liquid from the mirror, as described above.

Figure 3:
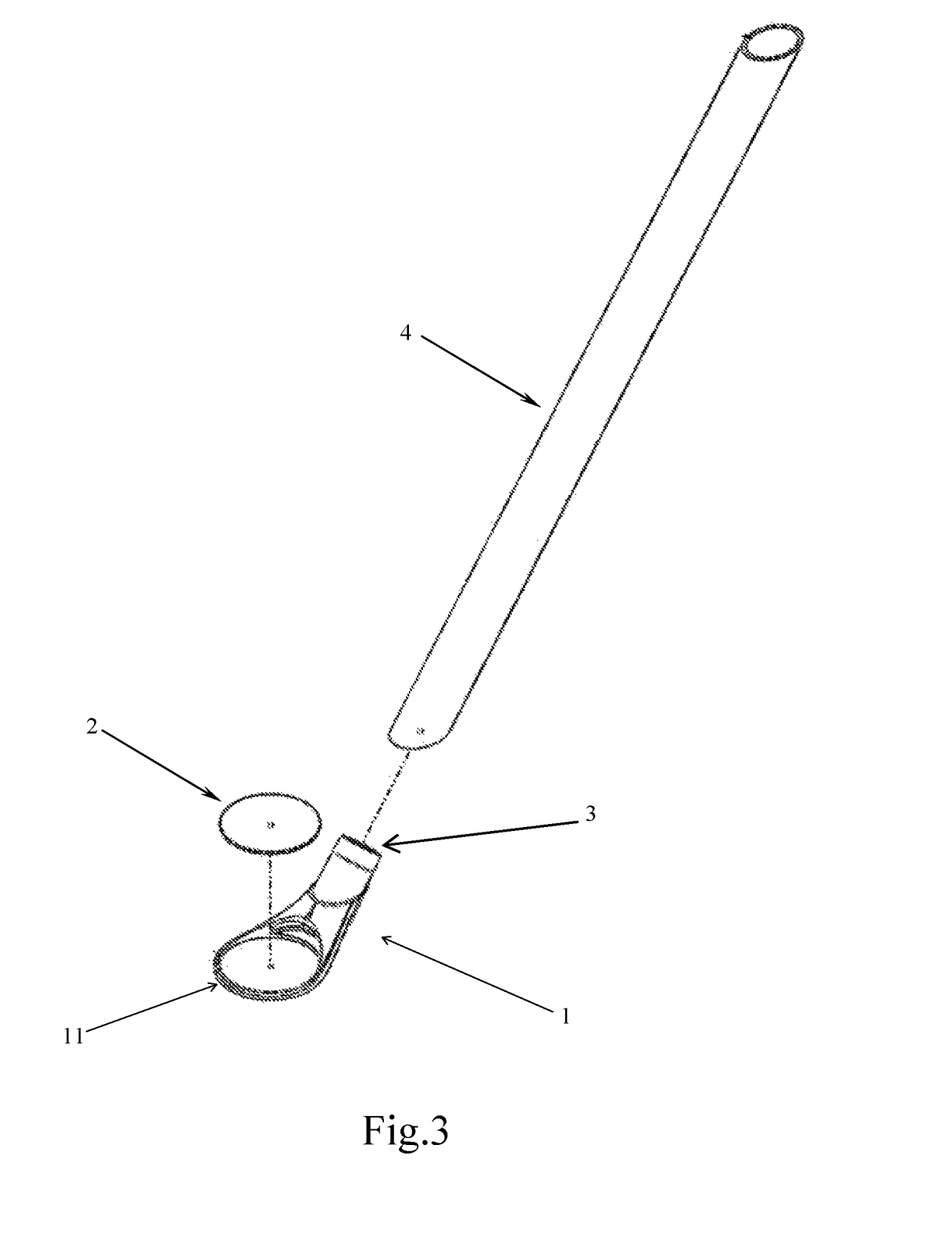
FIG. 3 is a perspective front view of the dental suction-mirror tool with a suction tube as handle according to one embodiment of the invention.

Reference is now made to FIG. 3 showing the dental suction-mirror tool with a handle. This particular disposable dental mirror tool comprises mirror frame 1, mirror 2, and cylindrical suction tube base 3 for accepting a standard suction tube/handle 4. Bended mirror frame 1 can be easily attached to and detached from handle/suction tube 4. Alternatively, all parts may constitute a disposable single continuous unit or piece of plastic. In one embodiment, frame 1 and bottom 10 constitute a disposable piece of plastic.

Handle 4, as shown in FIG. 3, is used to manipulate the mirror. It may have any suitable geometrical shape and can be straight or curved. The handle may be flexible, smooth or contoured, and should be long enough to easily manipulate the mirror with one hand. A skilled artisan, given the benefits of the disclosure, will be able to select materials, geometries and dimensions for the handle suitable for an intended use. The suction tube base 3 is inserted and passed through suction tube/handle 4. Since mirror frame 1, with the cylindrical suction tube base 3, is bent at angle 5, the suction tube will be positioned at this very specific angle, and the suction will be optimal, as described above.

Figure 4:
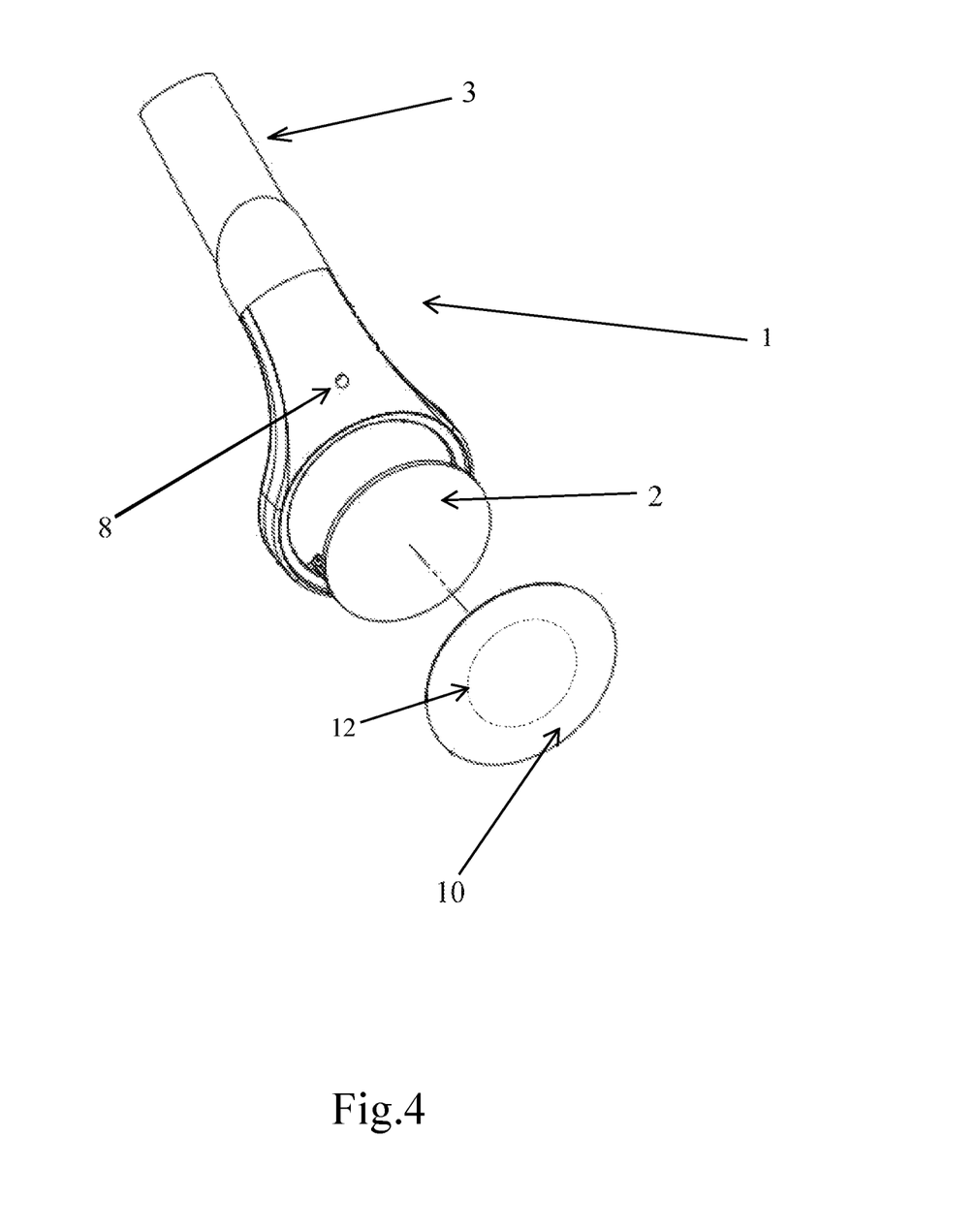
FIG. 4 is a perspective view from below of the dental suction-mirror tool according to one embodiment of the invention.
Figure 5:
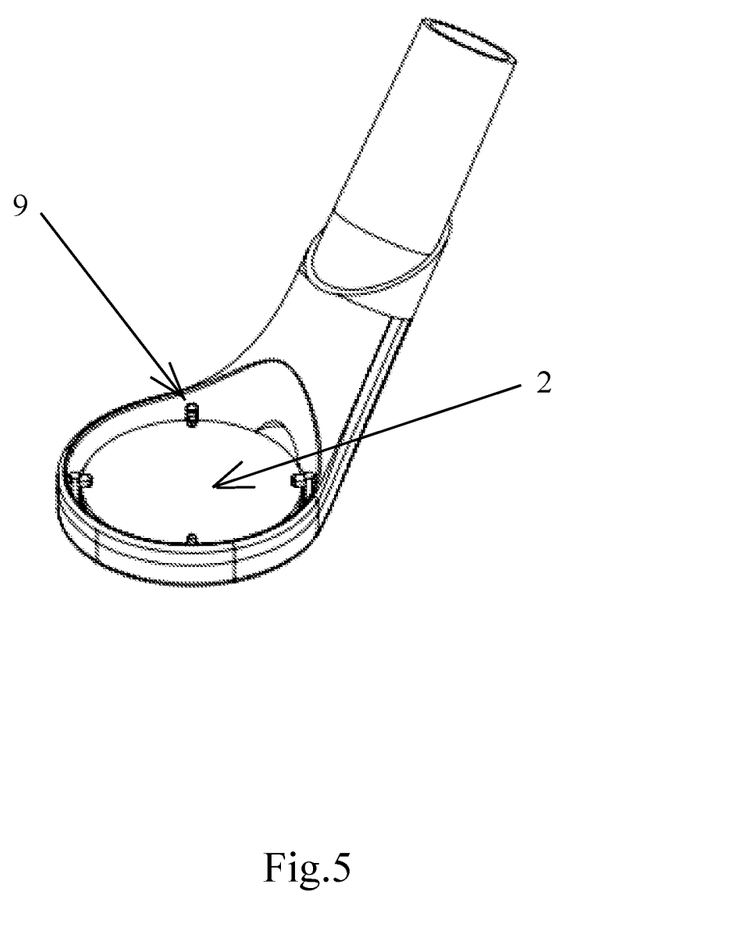
FIG. 5 is a perspective view from above of the dental suction-mirror tool depicted in FIG. 4.

Disposable mirror 2 may be a round sticker having a reflective side and an adhesive side with the attached double-side adhesive tape used to stick the disposable mirror to the frame bottom for use in a dental procedure. In a further aspect of the invention, disposable mirror 2 is made of glycol-modified polyethylene terephthalate (PETG), which is a clear and highly reflective thermoplastic polymer. The PETG mirrors are anti-fog, lightweight, biocompatible, flexible, impact resistant and commercially available, for example under trade names Plaskolite®, MirroPlast™, Vivak® and Soectar®. These mirrors have adhesive back with the double-side adhesive tape and custom masking on front and back. FIG. 4 and FIG. 5 show other embodiments of the invention, comprising frame bottom 10, mirror 2 sitting on said bottom 10 and kept within the frame by snaps 9; said mirror and said frame bottom preferably being embedded in a circular recess within the frame. The two openings, 7 and 8, evacuate fluids from the tool's environment in an efficient way, the front opening sucking the fluid across the mirror, and the back opening possibly removing accumulated liquids below the tool, thereby preventing overflow of the mirror surface. In a preferred embodiment of the invention, said mirror has a smaller diameter than said frame circular section into which it is set, allowing the sucked liquid to move also between the mirror edge and the frame to below the mirror surface, said frame bottom further being provided with as a circular ridge 12, concentric with the circular edge of the frame bottom and rising toward the mirror; said mirror 2 sits on the ridge 12, creating a free space between said mirror and said bottom 10, wherein a part of the sucked liquid moves from above the mirror surface via said space and via said front oblong opening to the suction tube; the clearance between said mirror edge and the frame circular section may be for example about 1 mm. Upon completion of the dental procedure, the dental mirror tool can be easily disposed.

In another aspect, the present invention relates to a method of simultaneously viewing in the patient's mouth and cleaning debris formed during dental procedures. The new method and tool can be used virtually in any dentist office or clinics and in any dental environment.

While certain features of the invention have been illustrated and described herein, many modifications, substitutions, changes, and equivalents will be apparent to those of ordinary skill in the art. It is, therefore, to be understood that the appended claims are intended to cover all such modifications and changes as fall within the true spirit of the invention.

The invention claimed is:

1. A disposable dental suction mirror tool, comprising:
   i) a mirror frame (1) made of a single plastic piece shaped to comprise:
      a) a circular section (11) for accommodating a circular mirror, defining a mirror plane;
      b) an oblong opening (7) adjacent to said circular section for evacuating fluids from said mirror, defining a front part of said frame;
      c) a cylindrical suction tube base (3) for inserting into a standard dental suction tube, the tube serving as a handle and connecting said dental tool with a vacuum source, said cylinder and said mirror plane forming an angle of between 50° and 60° ; and
      d) a circular, back opening (8) for evacuating fluids from behind and beneath said frame, defining a backside part of said frame;
   ii) a frame bottom (10) having a circular edge and located in said circular section for supporting said mirror; and
   iii) a planar anti-fog mirror (2) to be attached on said frame bottom in said circular section; said angle and said openings allowing for optimal liquid flow relative to the mirror plane and for effectively removing fluids and debris created during a dental procedure, thereby preventing the mirror from becoming non-reflective; and
   wherein said mirror has a smaller diameter than said frame circular section into which said mirror is set, allowing sucked liquid to move also between the mirror edge and the frame to below the mirror surface, said frame bottom further being provided with a circular ridge, concentric with said circular edge of the bottom and elevated toward the mirror; said mirror sits on the ridge, creating a free space between said mirror and said bottom, wherein a part of the sucked liquid moves from above the mirror surface via said space and via said front oblong opening to the suction tube.

2. The dental tool of claim 1, wherein said frame and said frame bottom constitute an integrated disposable plastic unit.

3. The dental tool of claim 1, wherein said frame bottom is attached to said round section by welding, for example by ultrasonic welding.

4. The dental tool of claim 1, wherein said mirror is provided with an adhesive layer and is attached to said frame bottom by the adhesive layer.

5. The dental tool of claim 1, wherein said circular section is provided with snaps, and said mirror is held in said frame by said snaps.

6. The dental tool of claim 1, wherein said front opening efficiently evacuates liquids from the surface of said mirror, and said back opening prevents accumulation of liquids behind and/or below the tool and sudden immersion of the mirror surface.

7. The tool according to claim 1, wherein the anti-fog mirror comprises a thermoplastic polymer.

8. The tool according to claim 7, wherein the polymer is glycol-modified polyethylene terephthalate (PETG).

9. The tool according to claim 1, allowing for simultaneous viewing in the patient's mouth and cleaning debris formed during dental procedures.

* * * * *